US008658705B2

(12) United States Patent
Thomas et al.

(10) Patent No.: US 8,658,705 B2
(45) Date of Patent: Feb. 25, 2014

(54) CARBON OXIDES REMOVAL

(75) Inventors: David Thomas, Perth, WA (US); Rod Travis, Perth, WA (US); Michael Moppert, Perth, WA (US); Christopher John Kalli, Perth, WA (US); Gerald M. Elphingstone, Jr., Perth, WA (US); David L. Charlesworth, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/535,067

(22) Filed: Jun. 27, 2012

(65) Prior Publication Data

US 2014/0005284 A1     Jan. 2, 2014

(51) Int. Cl.
*C07C 27/00* (2006.01)
(52) U.S. Cl.
USPC ............. 518/700; 518/703; 518/704
(58) Field of Classification Search
USPC .......................... 518/700, 703, 704
See application file for complete search history.

(56) References Cited

U.S. PATENT DOCUMENTS

2003/0191197 A1*  10/2003  O'Rear ............. 518/704
2011/0237689 A1*   9/2011  Bae et al. ........... 518/702

FOREIGN PATENT DOCUMENTS

WO    WO 2010/004300    *  1/2010

* cited by examiner

Primary Examiner — Jafar Parsa
(74) Attorney, Agent, or Firm — Carlos L. Hanze

(57) ABSTRACT

A process for reducing the carbon oxide content in natural gas, by producing a carbon oxide containing natural gas from a geological formation through a natural gas delivery system; providing a reaction zone containing at least one catalyst suitable for hydrocarbon conversion in the natural gas delivery system; introducing hydrogen into the carbon oxide containing natural gas to form a reaction mixture; and passing the reaction mixture to the catalyst in the reaction zone to convert at least a portion of the carbon oxides in the natural gas to hydrocarbons.

19 Claims, 7 Drawing Sheets

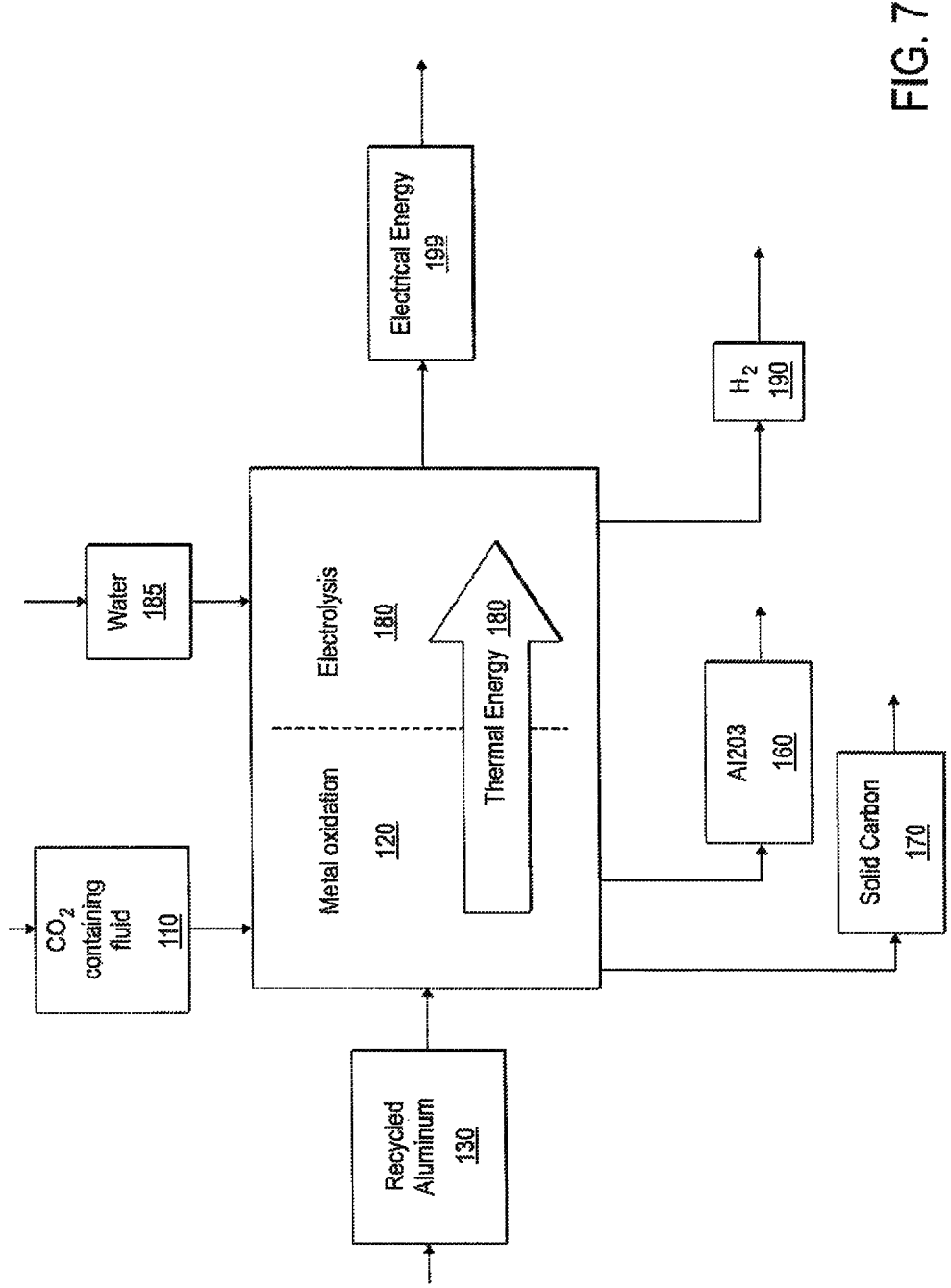

CARBON OXIDES REMOVAL

FIELD OF THE INVENTION

The present invention is directed to a system and process for removing carbon oxides, including carbon monoxide and carbon dioxide, from natural gas.

BACKGROUND OF THE INVENTION

Natural gas fields that are currently being produced frequently contain acid gases, in addition to the methane and decreasing amounts of higher hydrocarbons that are normally associated with natural gas production. Acid gases which are often encountered include one or more of $CO_2$, CO, hydrogen sulfide, carbonyl sulfide, carbon disulfide, mercaptans, sulfides and aromatic sulfur compounds. Processing and handling natural gas that contains acid gas contaminants present corrosion, handling and environmental problems that are generally addressed with high cost equipment and special procedures, often with additional energy costs involved.

Natural gas fields containing high amounts of carbon oxides are particularly costly and difficult to produce. Natural gas fields that contain greater than 70 vol. % carbon oxides are known. Low temperature liquefaction of such natural gas requires almost quantitative carbon oxide removal prior to the liquefaction step. The operator is thus faced with the challenges of removing that amount of carbon oxides in a cost effective process and disposing it in an environmentally responsible manner. Subterranean injection of carbon oxides is known, but it is neither easy, nor foolproof, nor cheap. Carbon oxide reaction schemes present other difficulties. An improved method of handling carbon oxide containing natural gas is desired.

SUMMARY OF THE INVENTION

The present integrated process is directed to removing carbon oxides from a carbon oxide containing fluid. The integrated process is further directed to methods for producing hydrogen for use in carbon oxide mitigation, in a thermally effective manner. In one embodiment, the process includes an electrolysis step for generating hydrogen for the process, and a thermal step for supplying heat to the electrolysis step while converting carbon oxides. Accordingly, the process comprises reacting carbon oxides with an active metal at an elevated temperature and producing thermal energy; and supplying at least a portion of the thermal energy to an electrolysis process, and recovering hydrogen.

In one embodiment, the process includes a separation step for removing carbon oxides from a carbon oxide containing fluid prior to treatment in the thermal step. Accordingly, the process comprises separating a carbon oxide containing natural gas into a carbon oxide rich fluid and a carbon oxide depleted natural gas; contacting the carbon oxide rich fluid with an active metal at elevated temperature and producing thermal energy and molecular carbon; supplying at least a portion of the thermal energy to an electrolysis process conducted at an elevated temperature, for producing at least hydrogen from electrolysis of water or brine; and contacting at least a portion of the hydrogen with carbon oxides to form hydrocarbons.

In one such embodiment, the carbon oxides which are converted to form hydrocarbons are produced from the carbon oxide containing natural gas. In another such embodiment, at least a portion of the hydrogen produced from the electrolysis of water is contacted with the carbon oxides in the presence of a catalyst to form hydrocarbons. In another such embodiment, the hydrocarbons that are formed include methane. In another such embodiment, at least a portion of the carbon oxide depleted natural gas is converted to a liquid phase.

In one embodiment, the process includes subjecting a carbon oxide containing fluid to hydrocarbon synthesis prior to a separation step. Accordingly, in one such embodiment, the process comprises supplying a carbon oxide containing natural gas, in combination with $H_2$ to a hydrocarbon synthesis zone; contacting the carbon oxide containing natural gas and hydrogen in the presence of a catalyst in the hydrocarbon synthesis zone to form hydrocarbons and a carbon oxide reduced natural gas; supplying the hydrocarbons and carbon oxide reduced natural gas to a separation zone and recovering a carbon oxide rich fluid and a carbon oxide depleted natural gas; contacting at least a portion of the carbon oxide rich fluid with an active metal at elevated temperature and producing thermal energy and molecular carbon; supplying at least a portion of the thermal energy to an electrolysis process conducted at an elevated temperature, for producing at least hydrogen from electrolysis of water or brine; and contacting at least a portion of the hydrogen produced from electrolysis with carbon oxides to form hydrocarbons.

In one embodiment, carbon oxides are removed in the natural gas delivery system that conducts the natural gas from a geological formation in which it occurs to surface facilities for processing and handling. This embodiment comprises producing a carbon oxide containing natural gas from a geological formation through a natural gas delivery system; providing a reaction zone containing at least one catalyst suitable for hydrocarbon conversion in the natural gas delivery system; introducing hydrogen into the carbon oxide containing natural gas to form a reaction mixture; passing the reaction mixture over the catalyst in the reaction zone to convert at least a portion of the carbon oxides in the natural gas; and producing a carbon oxide reduced natural gas.

In one embodiment, at least one catalyst suitable for hydrocarbon conversion is provided in a product manifold that transports natural gas from more than one well to surface facilities for processing and handling.

In one embodiment, the process includes treating a carbon oxide containing natural gas in a hydrocarbon synthesis step, and using a flue gas to generate the thermal energy for the electrolysis to produce hydrogen. Accordingly, the process comprises supplying a carbon oxide containing natural gas, in combination with $H_2$ to a hydrocarbon synthesis zone; contacting the carbon oxide containing natural gas and hydrogen with a catalyst in the hydrocarbon synthesis zone to form hydrocarbons and a carbon oxide reduced natural gas; contacting a flue gas with an active metal at elevated temperature and producing thermal energy and molecular carbon; supplying at least a portion of the thermal energy to an electrolysis process conducted at an elevated temperature, for producing at least hydrogen from electrolysis of water or brine; and contacting at least a portion of the hydrogen produced from electrolysis with carbon oxides to form hydrocarbons. In one such embodiment, the process further comprises liquefying at least a portion of the carbon oxide reduced natural gas.

In one embodiment, the process for contacting a carbon oxide containing fluid with an active metal at elevated temperature in a combustion zone of a reaction vessel, and producing hydrogen from electrolysis of water or brine in an electrolysis zone of the reaction vessel, wherein at least a portion of the heat generated within the combustion zone provides the thermal energy for maintaining the electrolysis zone at an elevated temperature.

BRIEF DESCRIPTION OF THE DRAWINGS

FIG. 1 through FIG. 7 illustrate embodiments of the process which includes reducing the carbon oxide content of natural gas.

DETAILED DESCRIPTION OF THE INVENTION

Figure 1:
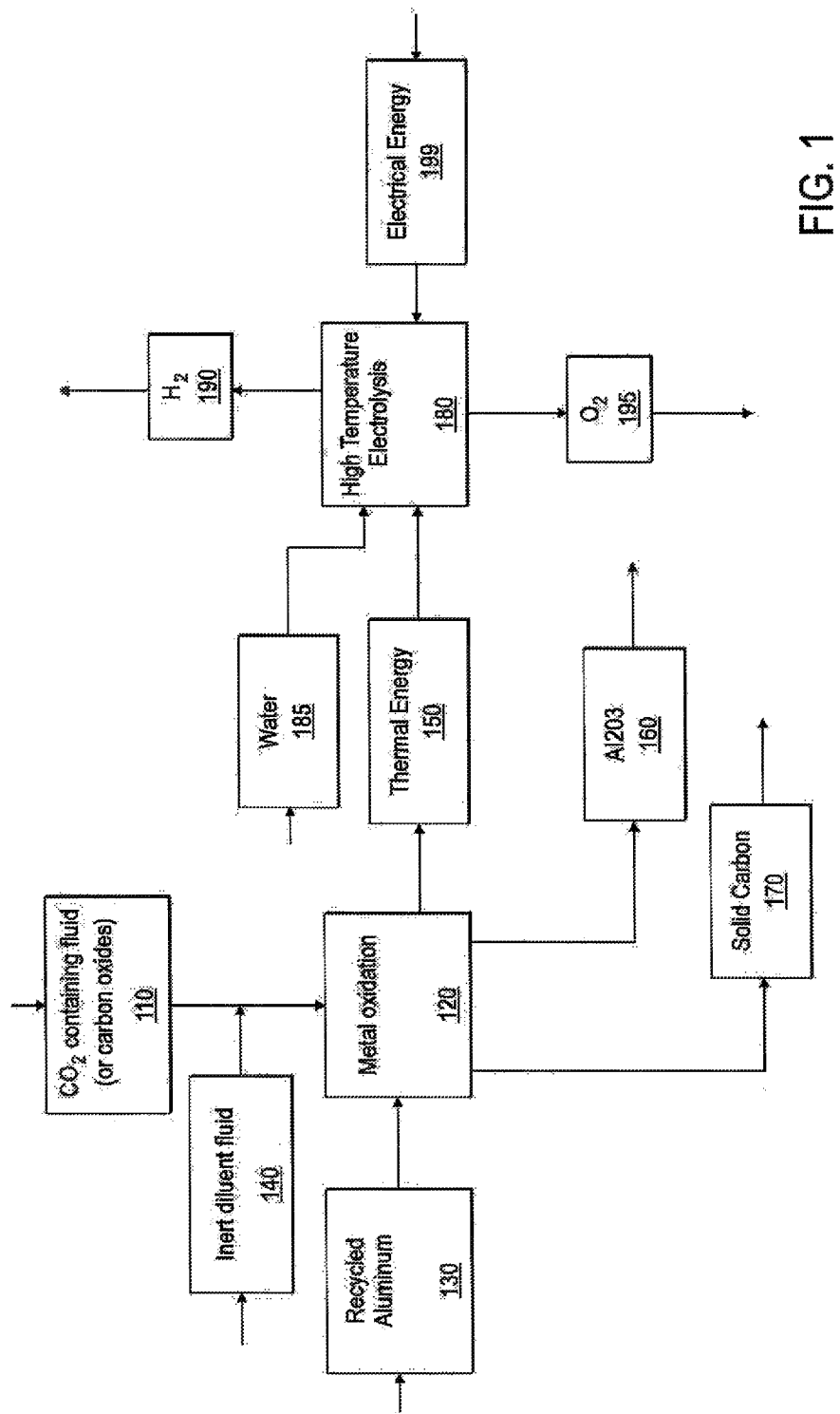

The present integrated process for producing hydrocarbons while converting carbon oxides involves the treatment of a gaseous fluid that contains carbon oxides. The process comprises an electrolysis step for converting carbon oxides to molecular carbon; the converted carbon oxides are thus removed as a potential greenhouse gas emission source. While $CO_2$ is an important contaminant that is converted in the process, other carbon oxides are also treated and removed as described. The carbon oxides are gaseous oxides, including, for example, carbon dioxide ($CO_2$) and carbon monoxide (CO) or combinations thereof. In one embodiment, carbon oxides contain in the range from 90 vol. % to 100 vol. % $CO_2$. In one embodiment, carbon oxides comprise $CO_2$ and CO in a volumetric ratio in the range from 99.9:0.1 to 50:50. In one embodiment, the carbon oxides comprise $CO_2$ and CO in a volumetric ratio in the range from 99.99:0.01 to 95:5. The carbon oxides are contained in a fluid that is gaseous at ambient temperature and pressure.

The carbon oxide containing gaseous fluid that is treated contains carbon oxides in a broad concentration range, depending on the source and the local requirements of the process. Natural gas that is suitable for treatment contains in the region of 1 vol. % to 75 vol. % carbon oxides. Other gases that are suitable for treatment, such as flue gas, contain in the range from 1 vol. % to 60 vol. % carbon oxides. In some cases, a suitable gas for treatment contains a diluent, such as an inert gas, added, for example, to moderate the temperature of the oxidation reaction. Alternatively, the carbon oxide containing gas stream is separated into at least a carbon oxide depleted fluid and a carbon oxide rich fluid. The carbon oxide rich fluid, which contains, in one embodiment, in the range from 30 vol. % to 100 vol. % carbon oxides, is passed to the metal oxidation step. In embodiments, the carbon oxide containing fluid also contains one or more other acidic contaminants, including, for example, hydrogen sulfide, carbonyl sulfide, carbon disulfide, mercaptans, sulfides and aromatic sulfur compounds. An exemplary carbon oxide containing fluid contains between 0 and 45 vol. % hydrogen sulfide. Another exemplary carbon oxide containing fluid contains between 5 and 40 vol. % hydrogen sulfide. In one embodiment, the carbon oxide depleted fluid is converted to liquefied natural gas.

Origin of Carbon Oxides

Flue Gas

In one embodiment, a flue gas is an input gas to the process, the flue gas containing the oxidation products from oxidation of carbonaceous material. Furnaces, boilers, and heaters, including process heaters, are suitable sources of the flue gas. Industries that would benefit from the process include petrochemical, petroleum, crude oil and gas producing, heat generating and mining industries, and the like. In one embodiment, the flue gas is obtained from a power producing plant, such as a coal fired, or oil fired or natural gas fired power plant, a steel plant, a petrochemical plant, a refinery, a cement plant, or any other plant that produces a flue gas. In addition to the carbon oxides, the flue gas may contain oxides of sulfur and nitrogen, including sulfur dioxide, nitric oxide and nitrogen dioxide.

Natural Gas

In one embodiment, the carbon oxides are present as a contaminant of natural gas. Natural gas, which contains methane and varying amounts of heavier hydrocarbons, may be recovered from geological formations as a mixture with carbon oxides and other contaminant gases. Natural gas containing as much as 75 vol. % carbon oxides, or more, is known. Indeed, gases containing up to 100% carbon oxides may be treated by the process.

Carbon Oxide Containing Fluid

Carbon Oxide Separation and Concentration

In one embodiment, the carbon oxides are provided to the process in combination with flue gas or natural gas, without preliminary separation. In another embodiment, the carbon oxides are separated from the other gases with which they are associated. Various carbon oxide removal processes are known. These include absorption processes such as those using an amine solvent solution (e.g. methyl-diethanol amine and water), cryogenic processes, adsorption processes such as pressure swing adsorption (PSA) and thermal swing adsorption (TSA), and membrane-based processes.

Membrane Separation

Membranes with a high selectivity for acidic contaminants in the gaseous fluid, such as carbon dioxide and hydrogen sulfide, are known. The selectivity is defined as the ratio of the acidic contaminants permeability over the permeability of the hydrocarbons as measured in single gas experiments. An exemplary membrane for use in the process has a selectivity of between 10 and 200. Another exemplary membrane has a selectivity of between 20 and 150. A membrane of this type includes, for example, a membrane chosen from a polyethylene oxide based membrane, a polyethylene oxide based membrane comprising block-copolymers, a cross linked polyethylene oxide based membrane, a polyimide or polyaramide based membrane, a cellulose acetate based membrane, a zeolite based membrane, a silica-alumina phosphate based membrane, such as SAPO-34, a micro-porous silica membrane or a carbon molecular sieve membrane.

Amine Separation

In an embodiment, the retentate from the membrane separation is further contacted with an amine solvent, in an amine separation step, for extracting at least a portion of the carbon oxides remaining the in the retentate into the amine solvent. Amine separation facilities for are well known. An exemplary amine solvent is methyldiethanol amine. The carbon oxide containing fluid that is supplied to the separation process will have a pressure between 30 and 120 bara. An exemplary separation process involves treating a carbon oxide containing fluid having a pressure between 40 and 100 bara; a second exemplary separation process treats a carbon oxide containing fluid having a pressure between 50 and 90 bara. The carbon oxide containing fluid has a temperature between −30 and 120° C. One exemplary fluid has a temperature between −20 and 100° C. A second exemplary fluid has a temperature between 0 and 50° C. The carbon oxide rich fluid that is produced from a membrane separation and supplied to the metal oxidation step generally has a pressure between 1 and 30 bara; an exemplary fluid has a pressure between 5 and 25 bara.

Metal Oxidation

In carrying out one step of the process, an active metal is reacted with carbon oxides at an elevated temperature. During the reaction, the active metal is converted to an oxide and the carbon oxides are reduced. In the case of carbon dioxide as the reactant, carbon monoxide and carbon are reduced products. In the case of carbon monoxide as the reactant, carbon is the reduced product. While some carbon monoxide may be produced during the reaction, the process is generally operated to convert a high proportion of the carbon oxides to molecular carbon (i.e. solid carbon).

In one embodiment, the reactions of the metal with the carbon oxides may be illustrated as follows. At least a portion of the carbon oxides contained in the carbon oxide containing fluid is believed to react by the following stoichiometry:

$$CO_2 + 2M \rightarrow 2MO + C \quad (a)$$

Likewise, at least a portion of the carbon monoxide contained in the fluid, or that is generated during the metal oxidation step, is believed to form molecular carbon by the following stoichiometry:

$$CO + M \rightarrow MO + C \quad (b)$$

wherein $CO_2$ and $CO$ represent carbon dioxide and carbon monoxide respectively, M represents a metal, MO represents a metal oxide and C represents molecular carbon. Alternatively, at least a portion of the carbon dioxide contained in the fluid, or that is generated during the metal oxidation step, is believed to form CO by the following stoichiometry:

$$CO_2 + M \rightarrow MO + CO \quad (c)$$

The active metal that is suitable for the process is any metal that reacts with carbon oxides with the generation of heat. In one embodiment, the active metal is aluminium; in another embodiment, magnesium; in another embodiment, iron; in another embodiment, calcium; in another embodiment, zinc. In a further embodiment, the active metal is selected from the group consisting of aluminium, magnesium, iron, calcium, zinc, and combinations thereof. The active metal is provided to the oxidation process as a pure metal or in a mixture, alloy or blend with at least one other material, the other material having some, or in the alternative no, activity for reacting with the carbon oxide. The metal that is provided to the oxidation process is of a form that is conducive to reaction, e.g. a powder, a ribbon, a sheet, a foil, a rod, or a brick. Scrap metal is also a suitable source of the active metal.

To initiate the process, the reactive metal is heated to at least an initiation temperature, at which the metal ignites in a fluid of flowing carbon oxide containing gas. The ignition temperature depends on the metal, on the concentration of carbon oxides in the flowing gas fluid, and on the inlet temperature of the flowing gas fluid. Under some conditions, at least, the ignition temperature is above 500° C. In one embodiment, the metal reacts with the carbon oxides at a temperature in the range from 500° C. to 2000° C. In one embodiment, the metal reacts with the carbon oxides at a pressure in the range from 1 bara to 100 bara (i.e. atmospheric pressure to 100 atmospheres pressure).

The metal oxidation step is exothermic, and, under some conditions at least, high exothermic. At least a portion of the thermal energy generated during the metal oxidation is recovered, for use in the electrolysis step that is a part of the integrated process. In one embodiment, the heat generated during oxidation is carried from the reaction by gas phase effluent from the oxidation step, at least a portion of which is exchanged with the electrolysis. Alternatively, the electrolysis step is conducted within the metal oxidation reaction zone; thermal energy from oxidation is passed directly to electrolysis. In another embodiment, the water that is supplied to the electrolysis process passes first through the metal oxidation process for heating.

The metal oxidation step also forms molecular carbon, which is collected from the oxidation step. In one embodiment, the molecular carbon passes from the reaction in the form of a powder, which is recovered using one or more known gas/solid process, such as, for example, a filter separation, a cyclone separation, an electrostatic separation, or a combination thereof.

Electrolysis

In one embodiment, the thermal energy generated in sequestering carbon oxides in the process is used by the process for generating hydrogen. In effect, the process for converting carbon oxides to hydrogen in the multistep process provides a method for converting a greenhouse gas into a fuel or reaction feedstock, including a reaction feedstock for the production of additional hydrocarbonaceous products. Alternative known or future developed heat sources may be used and are within the scope of the invention. This could include, e.g., solar energy or heat from other industrial processes. Alternative known or future developed sources of hydrogen are also within the scope of the invention.

At least a portion of the thermal energy generated during metal oxidation is provided to an electrolysis step, where electrolysis involves using an external circuit to produce a chemical change. The electrolysis is conducted at elevated temperature to exploit an efficiency improvement with increasing temperature. In one embodiment, the high temperature electrolysis involves the disassociation of water into oxygen and hydrogen; the electrolysis is suitably conducted at a temperature such that the water participates in the electrolysis reactions in the vapor phase. In one embodiment, the electrolysis step is conducted at a temperature of greater than 100° C.; in another embodiment, the electrolysis step is conducted at a temperature in the range from 100° C. to 850° C. Using the thermal energy for other known or future developed uses, e.g., rankine cycle heat recovery, is within the scope of the invention.

Water Electrolysis

In one embodiment, water is a feedstock to the electrolysis process; products include $H_2$ and $O_2$ from the disassociation of the water. Because water electrolysis is increasingly endothermic with temperature, electricity demand can be significantly reduced, if the formation of hydrogen takes place at high temperatures. Product oxygen recovered from electrolysis may be used for oxidation within the process, may be removed from the process for other uses, or may be vented.

$CO_2$ Electrolysis

In one embodiment, carbon dioxide is a feedstock to the electrolysis process; products include CO and O2. The CO is useful, for example, as a feedstock to a hydrocarbon synthesis process. In one embodiment, methanol is a product of the synthesis process. In one embodiment, methane is a product. In one embodiment, higher hydrocarbons, including hydrocarbons having carbon numbers from $C_2$ (e.g. ethane) to $C_{100}$ comprise at least a portion of the products from hydrocarbon synthesis. In one embodiment, diethyl ether is a product. In one embodiment, alcohols comprise at least a portion of the products. In one embodiment, the hydrocarbon synthesis process is a Fischer Tropsch process.

$H_2O + CO_2$ Electrolysis

In one embodiment, a mixture of water and $CO_2$ is a feedstock to the electrolysis process; products include CO and $H_2$. In another embodiment, electrolysis of a mixture of water and $CO_2$, in the presence of a catalyst, produces hydrogen and methane. In one embodiment, the catalyst comprises nickel.

Chloroalkali Electrolysis

In one embodiment, the hydrogen produced for the hydrocarbon synthesis step of the integrated process is generated by a chloroalkali electrolysis process. Chloroalkali electrolysis is generally conducted in a membrane cell or a diaphragm cell. In the membrane cell, the anode and cathode are separated by an ion-permeable membrane. Saturated brine is fed to the compartment with the anode. A DC current is passed through the cell and the NaCl splits into its constituent components. The membrane passes Na+ ions to the cathode compartment, where it forms sodium hydroxide in solution. The membrane allows only positive ions to pass through to prevent the chlorine from mixing with the sodium hydroxide. The chloride ions are oxidized to chlorine gas at the anode, which is collected, purified and stored. Hydrogen gas and hydroxide ions are formed at the cathode. A membrane cell is used to prevent the reaction between the chlorine and hydroxide ions.

In the diaphragm cell process, there are two compartments separated by a permeable diaphragm, often made of asbestos fibers. Brine is introduced into the anode compartment and flows into the cathode compartment. Similarly to the Membrane Cell, chloride ions are oxidized at the anode to produce chlorine, and at the cathode, water is split into caustic soda and hydrogen. The diaphragm prevents the reaction of the caustic soda with the chlorine. A diluted caustic brine leaves the cell. The chlorine contains oxygen and must often be purified by liquefaction and evaporation.

Hydrocarbon Synthesis

In the integrated process, hydrogen is used for hydrocarbon synthesis, in which methane and/or higher hydrocarbons are synthesized from reaction of $H_2$ with CO and $CO_2$. In one embodiment, $H_2$ used in the process is produced from one of a number of sources, including methane (and higher hydrocarbon) reforming, refinery processing and electrolysis. Applications of the integrated process that include an electrolysis step employ at least a portion of the hydrogen generated from electrolysis in the hydrocarbon synthesis step.

Carbon oxides that are used as a reactant for hydrocarbon synthesis is present in the flue gas or natural gas that is contaminated with carbon oxides (i.e., the carbon oxide containing fluid). In one embodiment, the carbon oxide containing fluid is contacted with hydrogen in the presence of a catalyst to form hydrocarbons and to reduce the amount of carbon oxides in the fluid. Fluids having a carbon oxide concentration in the range from 5 vol. % to 100 vol. % are suitable as feedstocks for the hydrocarbon synthesis step. In another embodiment, the carbon oxide containing fluid is treated in a separation step, which removes at least a portion of the carbon oxides into a carbon oxide rich fluid that is reacted with hydrogen in the hydrocarbon synthesis step.

$CO_2$ is generally a major component of carbon oxide contamination of natural gas; CO is generally a minor component, though the concentration of CO in flue gas may reach percent levels in some situations for which the present integrated process finds applicability. CO for the hydrocarbon synthesis step is generally made available to the process in combination with hydrogen as syngas. Syngas is produced during partial oxidation of carbonaceous material, including methane. In one embodiment, the integrated process includes a methane reformer for producing syngas by partial oxidation of natural gas for use in hydrocarbon synthesis and the capture and conversion of carbon oxide. Alternatively, carbon monoxide is recovered from the natural gas, and combined with hydrogen to form the syngas.

Sabatier Reaction

In one embodiment of the integrated process, hydrogen is caused to react with $CO_2$ in a so-called Sabatier reaction to form hydrocarbons, including methane. The reaction is facilitated by the presence of a catalyst; catalysts comprising nickel, ruthenium or mixtures of the two are suitable for use in the hydrocarbon synthesis step. Some useful catalysts include an oxide substrate.

In one embodiment, the hydrocarbon synthesis step occurs at a reaction temperature in the range from 150° C. to 500° C.

The hydrocarbon synthesis reaction is exothermic; in one embodiment, thermal energy generated during the synthesis reaction is passed to the electrolysis reaction to support maintaining the elevated temperature electrolysis process.

Water Gas Shift Reaction

The water gas shift reaction, which involves the reaction of CO with $H_2O$ to form $CO_2$ and $H_2$, is useful in the process for preparing reactants to be used in the hydrocarbon synthesis step. In one embodiment, CO is injected into a natural gas that contains water vapor to increase the amount of hydrogen present in the natural gas. Catalysts such as transition metals, transition metal oxides (e.g. $Fe_3O_4$) and Raney copper are suitable catalysts for the process. In one embodiment, a two stage reaction sequence is employed, with a first high temperature stage at 350° C. in the presence of an iron oxide catalyst promoted with chromium oxide, and a second low temperature stage in the presence of a zinc oxide on aluminium oxide catalyst.

$CO_2$ Conversion in a Natural Gas Delivery System.

In one embodiment, a carbon dioxide containing natural gas is produced from a geological formation and passes to surface processing and handling at some location from the production well. A natural gas delivery system includes the equipment and means, including tubing and valving, for conducting natural gas from the geological formation to surface processing and handling facilities. The delivery tubing and system for delivering the natural gas from the geological formation, for final cleanup and purification, comprises a reaction zone for converting at least a portion of the carbon dioxide contained in the natural gas, via a hydrocarbon synthesis reaction.

In one embodiment, the reaction zone is provided to remove $CO_2$ as an environmental greenhouse gas from the natural gas. In one embodiment, the reaction zone is positioned within the natural gas delivery system at a location between the geological formation, where the natural gas enters the tubing of the delivery system, and facilities on the earth's surface for processing and handling the produced natural gas.

In one embodiment, at least a portion of the $CO_2$ is converted in the reaction zone into hydrocarbons, such as methane, in a hydrocarbon synthesis step. A material having catalytic activity for hydrocarbon synthesis is provided in the reaction zone to facilitate the synthesis. In one embodiment, the reaction zone contains a hydrocarbon synthesis catalyst for reacting $CO_2$ with $H_2$ to form methane. In one such embodiment, the catalyst is nickel; in another embodiment, ruthenium; in another embodiment, nickel-ruthenium. In another embodiment, reaction of CO and $H_2$ produces principally normal paraffin and alcohol products. Cobalt or iron, with or without a platinum promoter, are suitable catalysts. In one embodiment, the reaction involves a Fischer Tropsch reaction, for converting CO (or CO2 that is interconverted to CO) and hydrogen to paraffinic hydrocarbons and alcohols.

The water gas shift reaction, which interconverts water, $H_2$ and the carbon oxides is suitable for shifting the balance of reactants within the natural gas. The pressure and temperature of the reaction zone within the delivery system, at which the catalytic reaction occurs, is supplied by the conditions of the geological formation from which the natural gas is produced.

In one embodiment, a single reaction zone is provided in the process. In another embodiment, multiple reaction zones are provided, each containing a catalyst intended for a different reaction, whether it be a $CO_2+H_2$ reaction to yield methane, a $CO+H_2$ reaction to yield alcohols and paraffins, or whether it be a water gas shift catalyst for interconverting water, $H_2$, CO and $CO_2$. Multiple reaction zones are either adjacent each other, or separated. In one embodiment, the catalyst is coated or plated directly on the inner wall of the tubing in the delivery system. The tubing in a typical natural gas delivery system may be of considerable length; over the course of the passage of the natural gas through the delivery system, there is sufficient contact between the carbon dioxide molecules in the natural gas and the walls of the delivery tubing to facilitate the conversion of at least a portion of the carbon dioxide to hydrocarbons.

In another embodiment, the reaction zone within the natural gas delivery system includes a honeycomb monolith, with catalytically active metals being deposited on the interior channels of a honeycomb monolithic. Generally a monolith substrate has a large surface area to facilitate the catalytic conversion process. A honeycomb structure contains numerous channels, usually running parallel to each other along the length of the substrate. The channel width varies, often depending on the substrate material and applications for which it is used. These channels allow the natural gas containing the carbon dioxide to flow freely through the monolith with a minimum of pressure drop. While the natural gas flows through the channels of the substrate and contacts the catalytic metals deposited thereon, the carbon dioxide molecules are converted into hydrocarbons molecules via chemical reactions.

In another embodiment, the catalytic metals are deposited on a static mixer that is installed in the tubing in the natural gas delivery system. In another embodiment, catalytic metals are deposited on substrate beads, which are introduced into the reaction zone within a natural gas delivery system for converting the carbon dioxide contained therein. Typical shapes of the beads includes flutes, cylinders and spheres, with an effective diameter in the region from 0.01 inch to 1 inch. In one embodiment, the beads are sized to permit lifting, fluidization or transport of the beads in the flowing natural gas within the delivery system. In another embodiment, the beads are sized and positioned such that at least a portion of them are fixed in place, and the natural gas containing the carbon dioxide is permitted to flow around the individual beads and through the reaction zone containing the beads.

Example 1

In the exemplary process illustrated in FIG. 1, a carbon oxide containing fluid (110) is passed to a metal oxidation unit (120) for converting the carbon oxides to molecular carbon, and/or $CO_2$ to CO, while oxidizing an active metal (130) to form an oxide form of the metal. In one embodiment, the active metal comprises aluminum. In another embodiment, the active metal comprises magnesium. In one embodiment, the carbon oxide containing fluid is a natural gas; in another embodiment, a flue gas. In one embodiment, the carbon oxide containing fluid comprises $CO_2$; in another embodiment, it comprises CO; in another embodiment, it comprises a combination of $CO_2$ and CO. An inert diluent stream (140) may optionally be added to the carbon oxide containing fluid (110), prior to introducing the fluid to the oxidation step. The metal oxidation step produces thermal energy (150), along with metal oxide (160) and molecular carbon and/or CO, (170) products.

In the process, at least a portion of the thermal energy (150) is passed to an electrolysis process step (180). In one embodiment, the electrolysis step (180) is a high temperature electrolysis for electrolyzing water (185) into its elemental components, hydrogen (190) and oxygen (195). In another embodiment (not shown), the electrolysis step involves an chloralkali electrolysis of brine, to form hydrogen, sodium hydroxide and at least one chlorine containing fluid. Electrical energy (199) is also passed to the electrolysis step for conducting the electrolysis process.

Example 2

Figure 2:
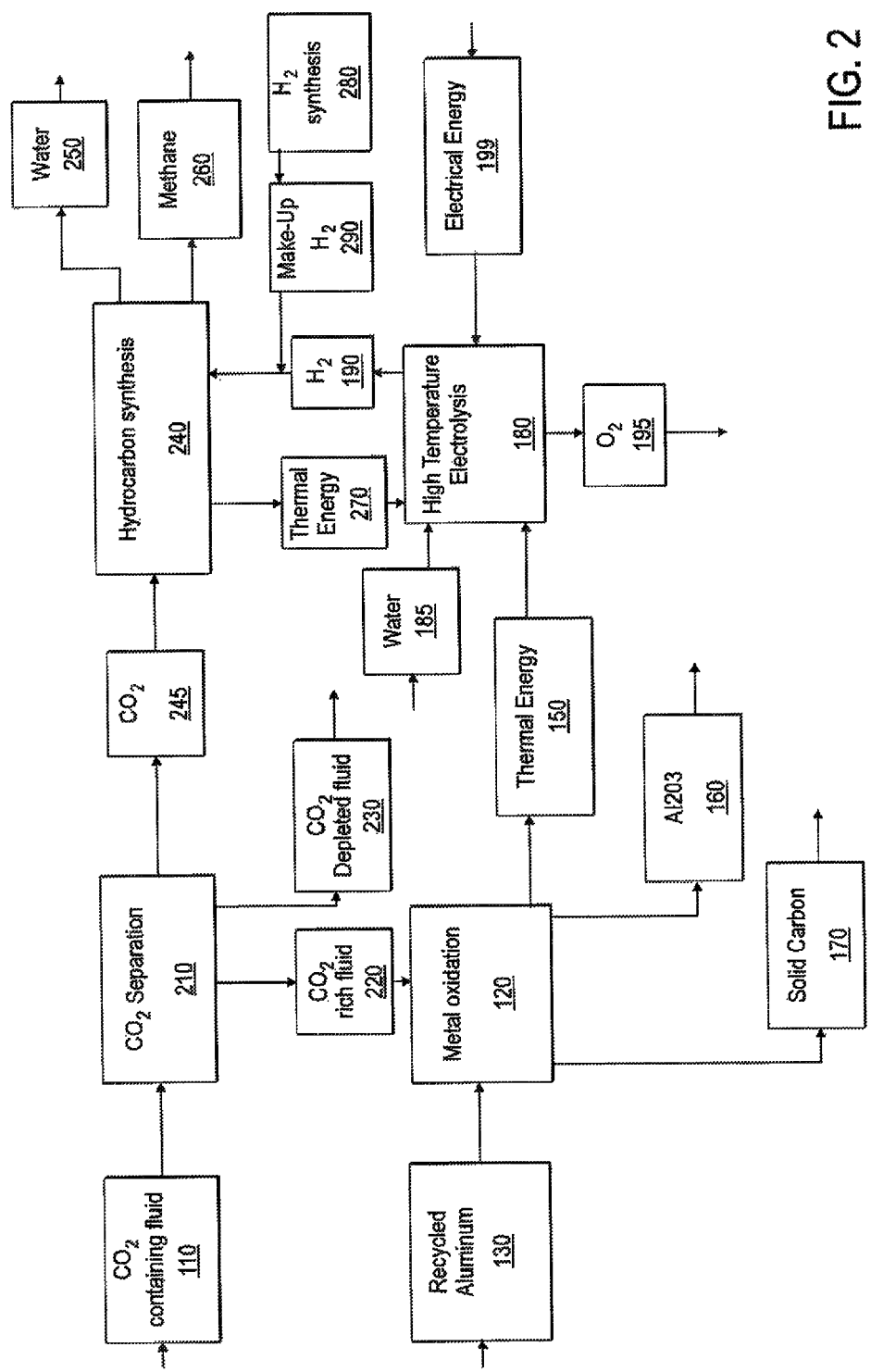

In the exemplary process illustrated in FIG. 2, a carbon oxide containing fluid (110) is passed to a separation step (210), for recovering at least a portion of the carbon oxides. At least two streams are produced in the separation step: a carbon oxide rich fluid (220) which contains at least a portion of the separated carbon oxides, and a carbon oxide depleted (230) fluid from which at least a portion of the carbon oxides have been removed. In one embodiment, the carbon oxide depleted fluid (230) is a natural gas. In one embodiment, the carbon oxide depleted natural gas (230) is passed to a liquefaction process for converting the natural gas to liquefied natural gas. In one embodiment, the separation step (210) includes a membrane separation; in another embodiment, an amine separation; in another embodiment, a combination of a membrane separation and an amine separation.

The carbon oxide rich fluid (220) is supplied to a metal oxidation step (120) for converting the carbon oxides in the fluid to molecular carbon, and/or $CO_2$ to CO. When maintained at a temperature above the ignition temperature, an active metal (130) reacts with carbon oxides in a highly exothermic reaction, forming at least an oxide (160) of the active metal and reducing the carbon oxides to molecular carbon and/or CO (170). Excess energy beyond that required to maintain the reaction in the metal oxidation step is available for use elsewhere in the integrated process. In the process, therefore, at least a portion of the thermal energy (150) generated during metal oxidation is passed to an electrolysis process step (180). In one embodiment, the electrolysis step (180) is a high temperature electrolysis for electrolyzing water (185) into its elemental components, hydrogen (190) and oxygen (195). In another embodiment (not shown), the electrolysis step involves a chloroalkali electrolysis of brine, to form hydrogen, sodium hydroxide and at least one chlorine containing fluid. Electrical energy (199) is also passed to the electrolysis step for conducting the electrolysis process.

Hydrogen (190) generated in the electrolysis process (180) is recovered for other uses in the integrated process. In one embodiment, the integrated process comprises a hydrocarbon synthesis step (240), for converting the hydrogen (190) and carbon dioxide (245) into hydrocarbons, e.g. methane. Carbon oxides from one or more of a number of sources, both from within and from outside of the integrated process, are suitable as a feedstock for the hydrocarbon synthesis step, including, for example, a portion of the carbon oxide containing fluid (110), a portion of the carbon oxide rich fluid (220), a portion of the carbon oxide depleted fluid (230), a separate carbon oxide containing fluid (245) produced during the separation step (210), a carbon oxide containing natural gas, and combinations thereof. During the catalytic conversion of $CO_2$ and $H_2$ in the hydrocarbon synthesis step (240), at least one hydrocarbon product (260) is produced, along with a water byproduct stream (250). In one embodiment, $CO_2$ react with $H_2$ over a nickel catalyst, a ruthenium catalyst, or a nickel-ruthenium catalyst to form methane. In one embodiment, at least a portion of the thermal energy (270) from the exothermic reactions during hydrocarbon synthesis (240) is passed to the electrolysis step (180).

Example 3

Figure 3:
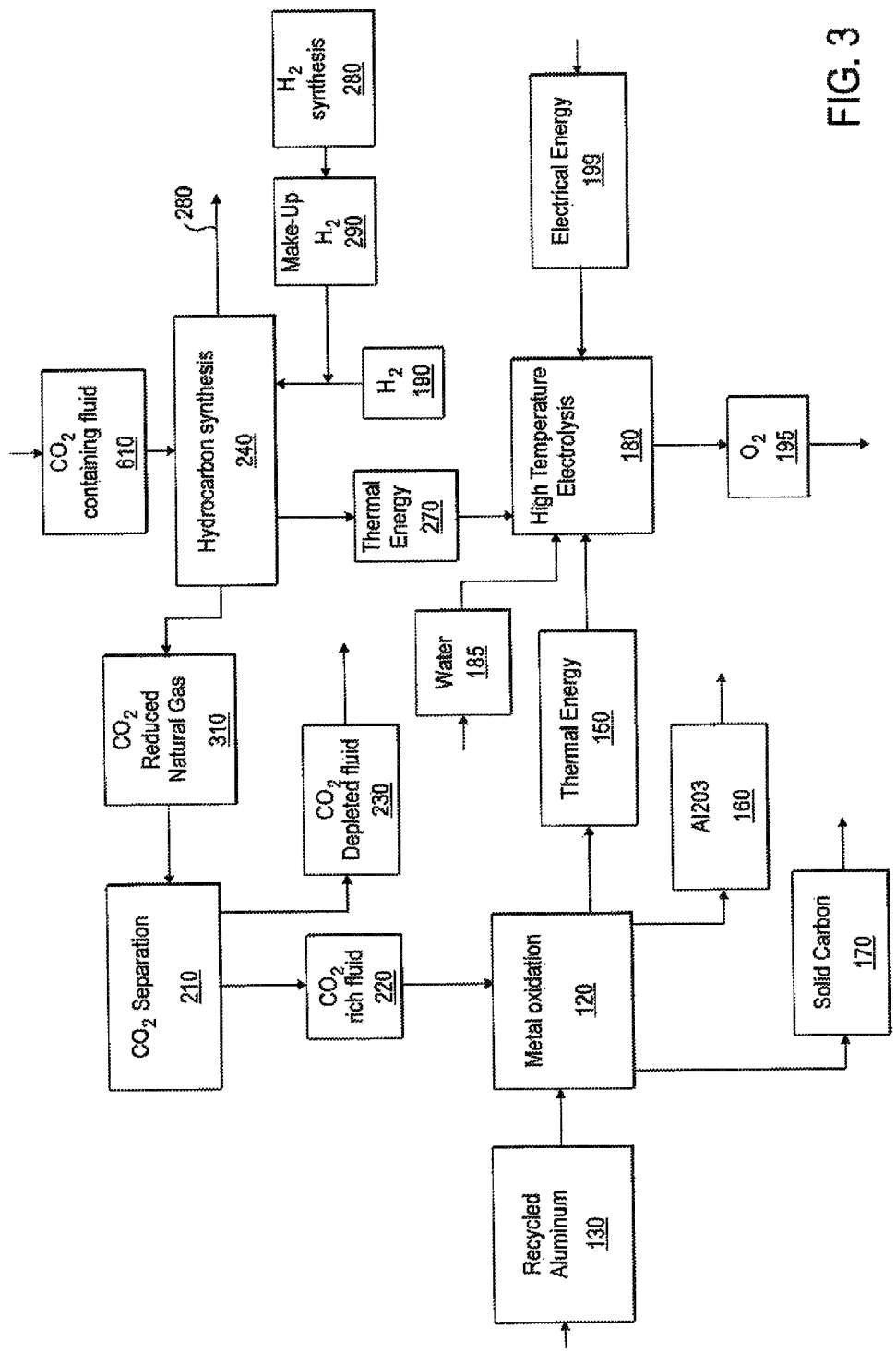

In the exemplary process illustrated in FIG. 3, a carbon oxide containing fluid (110), such as a natural gas, is passed to a hydrocarbon synthesis step (240) for converting at least a portion of the carbon dioxide contained therein into hydrocarbons (260) (e.g. methane) via reaction with hydrogen (190). At least a portion of the hydrogen (190, 290) which is supplied to the hydrocarbon synthesis step (240) is produced in an electrolysis step (180). In one embodiment, additional hydrogen (290) for synthesis is supplied from one or more additional sources (280), either from within or from outside of the integrated process.

In the embodiment illustrated in FIG. 3, methane that is formed during hydrocarbon synthesis is passed to a separation step (210) in combination with a carbon oxide reduced natural gas (310). In the separation step (210), at least a portion of the carbon oxides that remain in the natural gas following the hydrocarbon synthesis step (240) are separated into a carbon oxide rich fluid (220); a carbon oxide depleted fluid (230) is also recovered. In one embodiment, the carbon oxide depleted fluid comprises natural gas, and the carbon oxide depleted natural gas (230) is passed to a liquefaction process for converting the natural gas to liquefied natural gas.

The carbon oxide rich fluid (220) is supplied to a metal oxidation step (120) for converting the carbon oxides in the fluid to molecular carbon, and/or $CO_2$ to CO (170), and further converting at least one active metal (130) to at least one metal oxide (160). In the process, at least a portion of the thermal energy (150) generated during metal oxidation is passed to an electrolysis process step (180). In the embodiment illustrated in FIG. 3, thermal energy (270) generated during hydrocarbon synthesis is also passed to the electrolysis process step (180). In one embodiment, the electrolysis step (180) is a high temperature electrolysis for electrolyzing water (185) into its elemental components, hydrogen (190) and oxygen (195). In another embodiment (not shown), the electrolysis step involves a chloroalkali electrolysis of brine, to form hydrogen, sodium hydroxide and at least one chlorine containing fluid. Electrical energy (199) is also passed to the electrolysis step for conducting the electrolysis process.

Example 4

Figure 4:
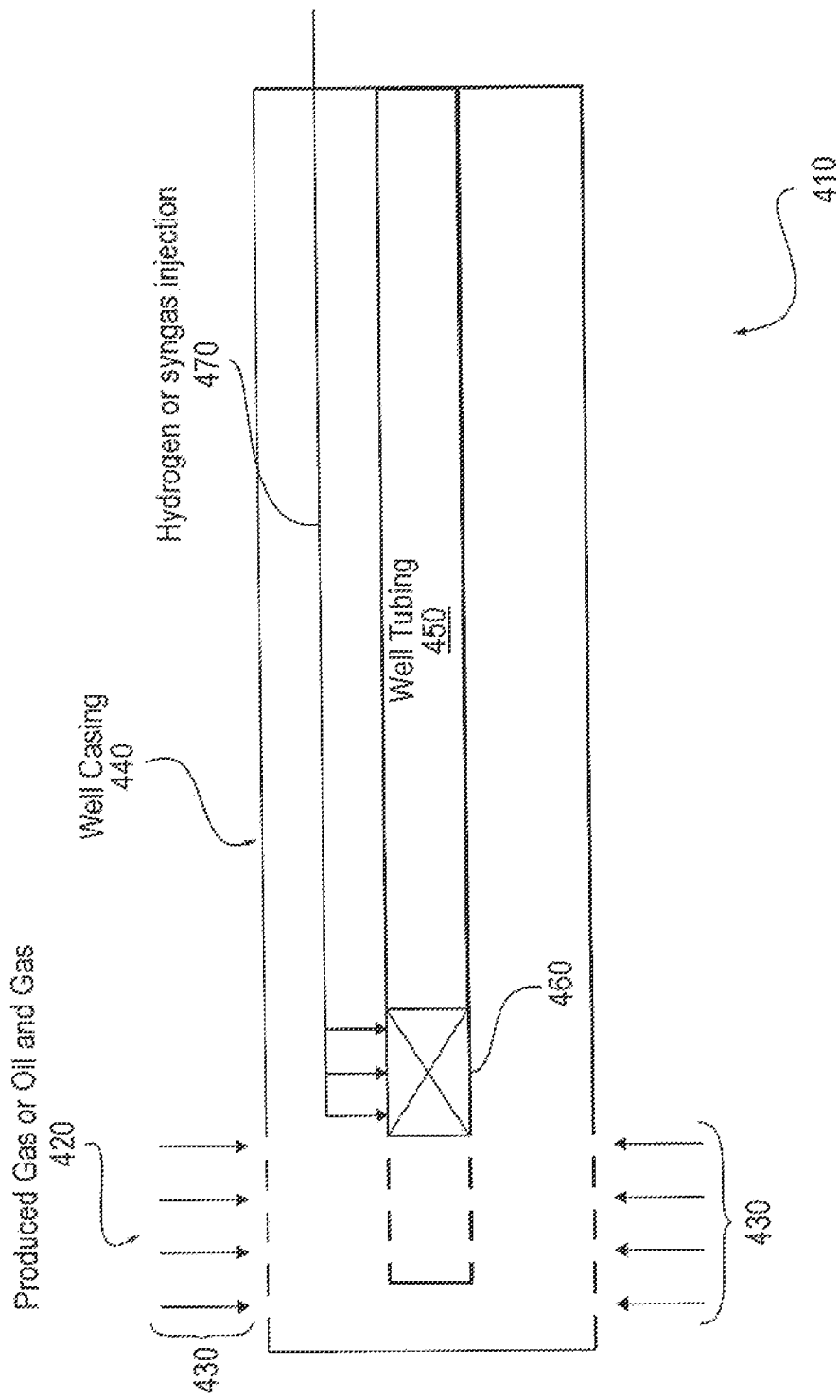

FIG. 4 illustrates a hydrocarbon synthesis reaction zone (410) in a natural gas (or a crude oil containing natural gas) production system. In the exemplary process illustrated in FIG. 4, a carbon oxide containing natural gas (420) is produced from a geological formation through perforations (430) in a well casing (440) and into well tubing (450). A reaction zone (460) for converting at least a portion of the carbon oxides contained in the natural gas is included in the well tubing. The reaction zone (460) includes a catalyst for the $CO_2$ conversion. In one embodiment, the catalyst is plated or coated to the inner wall of the well tubing; in another embodiment, it is provided on beads within a fixed or fluidized catalyst bed; in another embodiment, it is included in a fixed bed static mixer within the well tubing; in another embodiment, it is included in a monolith structure within the well tubing; in another embodiment, it is provided to the well tubing in any combination of these.

The carbon oxide content in the natural gas is reduced by conversion to hydrocarbons in one or a series of chemical conversion processes. In one embodiment, reaction of $CO_2$ with $H_2$ is forms methane. Nickel and ruthenium, taken alone or in combination, are suitable catalysts. In another embodiment, reaction of CO and $H_2$ produces principally normal paraffin and alcohol products. Cobalt or iron, with or without a platinum promoter, are suitable catalysts. The water gas shift reaction, which interconverts water, $H_2$ and the carbon oxides is suitable for shifting the balance of reactants within the natural gas.

$H_2$, CO or syngas (mixture of $H_2$ and CO (470)) is prepared in surface facilities is passed to the well tubing (450) that conducts the natural gas to the reaction zone (460) containing the catalyst. In one embodiment, at least a portion of the hydrogen is generated by electrolysis.

The pressure and temperature of the $H_2$/natural gas blend is determined, at least in part, by the reservoir conditions from which the natural gas originates. In the reaction zone the $CO_2$ in the natural gas reacts in the presence of the catalyst to form reaction products, e.g. methane. The product methane blends with the natural gas and the $CO_2$ concentration of the natural gas is reduced.

In one embodiment, natural gas leaving the reaction zone (460) passes to additional separation steps for further separation of remaining carbon oxides in the natural gas.

Example 5

Figure 5:
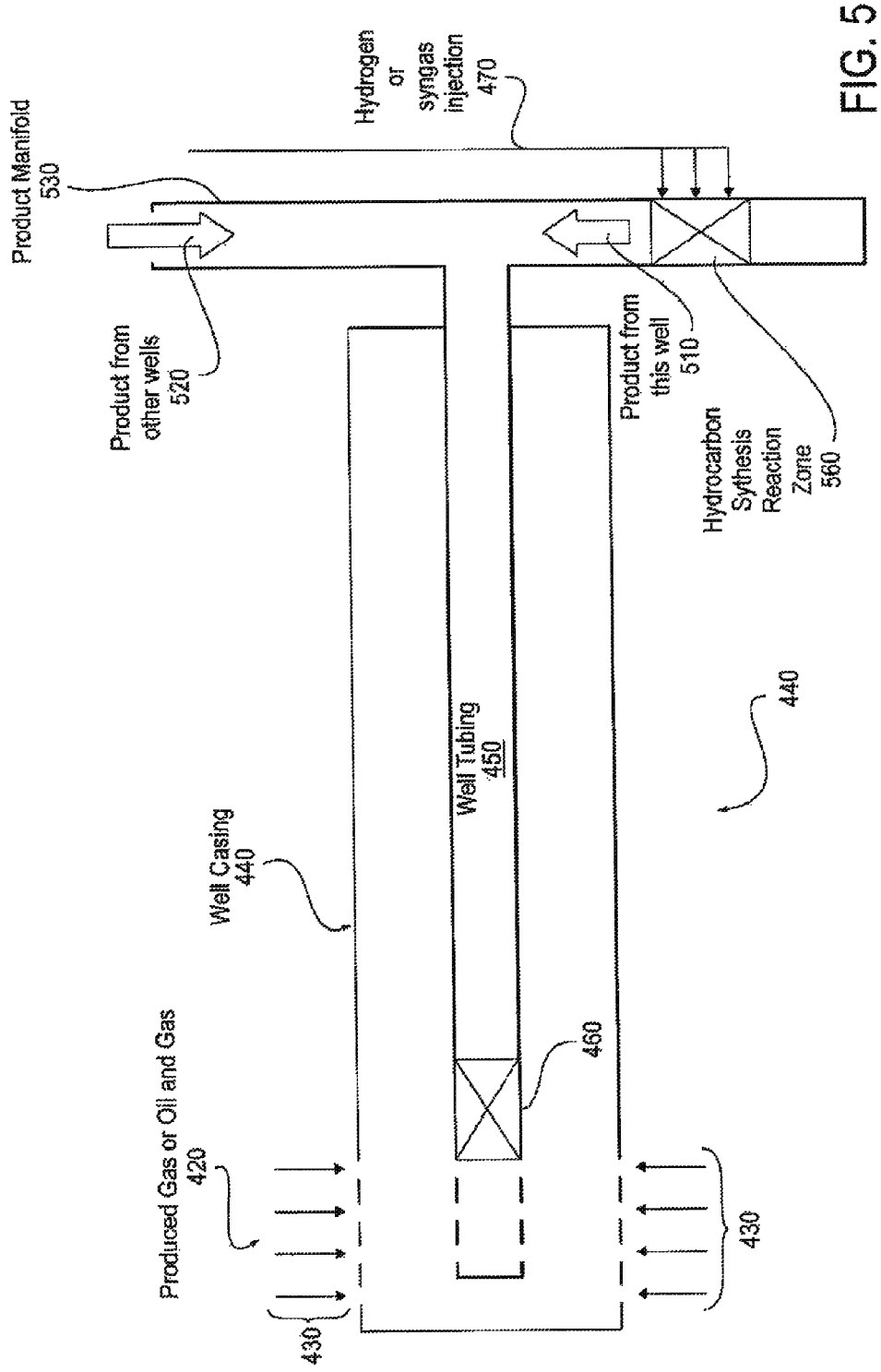

FIG. 5 illustrates a hydrocarbon synthesis reaction zone in the delivery system of a natural gas (or a crude oil containing natural gas) production system. In the exemplary process illustrated in FIG. 5, a carbon oxide containing natural gas (420) is produced from a geological formation through perforations (430) in a well casing (440) and into well tubing (450). From there the produced natural gas (510) from the well tubing combines with natural gas (520) produced in other wells in a product manifold (530), and the combination passes to a reaction zone (560) in the delivery tubing for converting at least a portion of the carbon oxides contained in the natural gas.

The reaction zone (560) includes a catalyst for the $CO_2$ conversion. In one embodiment, the catalyst is plated or coated to the inner wall of the well tubing; in another embodiment, it is provided on beads within a fixed or fluidized catalyst bed; in another embodiment, it is included in a fixed bed static mixer within the well tubing; in another embodiment, it is included in a monolith structure within the well tubing; in another embodiment, it is provided to the well tubing in any combination of these.

The carbon oxide content in the natural gas is reduced by conversion to hydrocarbons in one or a series of chemical conversion processes. In one embodiment, reaction of $CO_2$ with $H_2$ is forms methane. Nickel and ruthenium, taken alone or in combination, are suitable catalysts. In another embodiment, reaction of CO and $H_2$ produces principally normal paraffin and alcohol products. Cobalt or iron, with or without a platinum promoter, are suitable catalysts. The water gas shift reaction, which introconverts water, $H_2$ and the carbon oxides is suitable for shifting the balance of reactants within the natural gas.

$H_2$, CO or syngas (mixture of $H_2$ and CO (470)) is prepared in surface facilities is passed to the well tubing (450) that conducts the natural gas to the reaction zone (560) containing the catalyst. In one embodiment, at least a portion of the hydrogen is generated by electrolysis.

The pressure and temperature of the $H_2$/natural gas blend is determined, at least in part, by the reservoir conditions from which the natural gas originates. In the reaction zone the $CO_2$ in the natural gas reacts in the presence of the catalyst to form reaction products, e.g. methane. The product methane blends with the natural gas and the $CO_2$ concentration of the natural gas is reduced.

In one embodiment, natural gas leaving the reaction zone passes to additional separation steps for further separation of remaining carbon oxides in the natural gas.

Example 6

Figure 6:
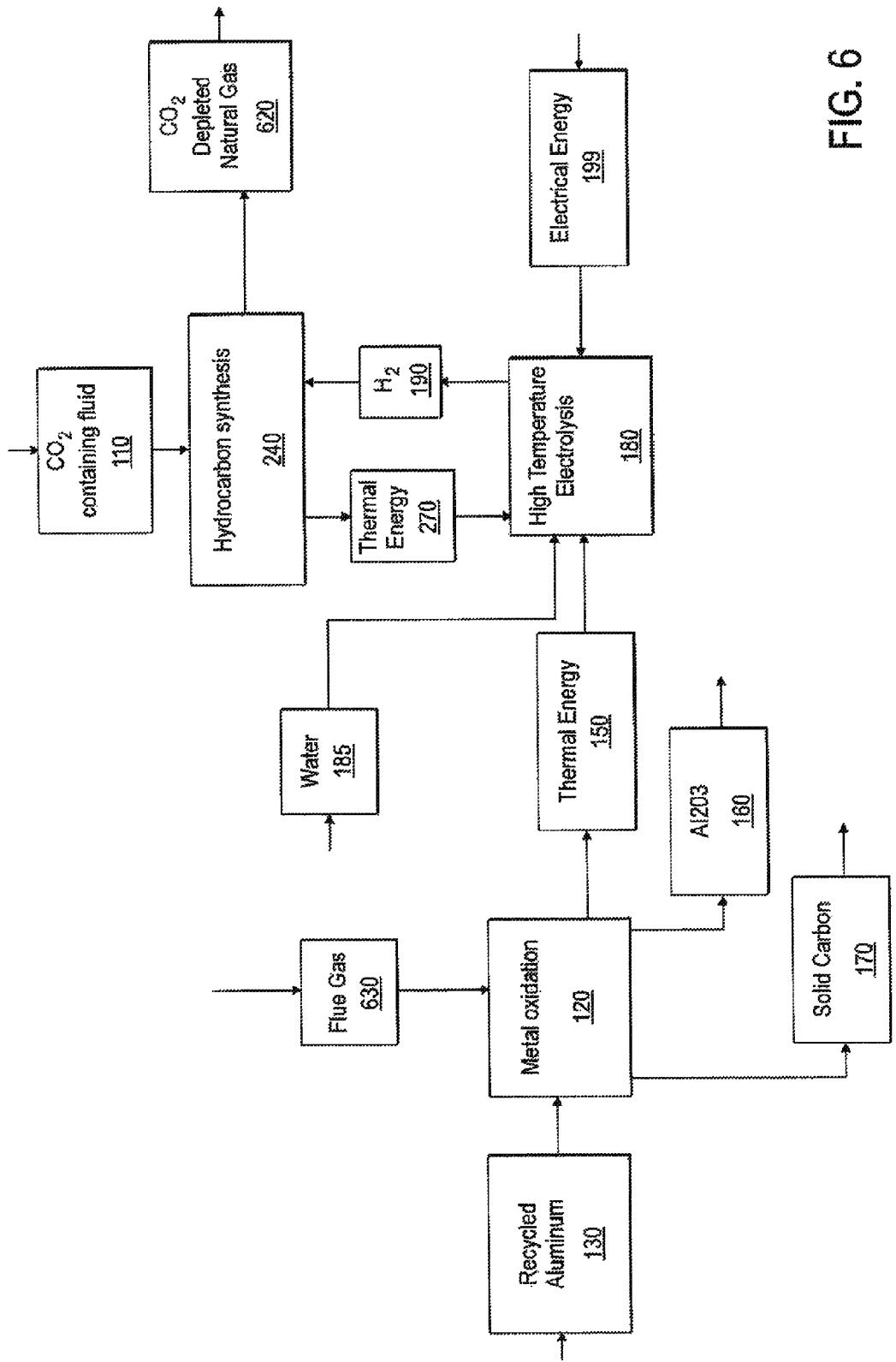

In the exemplary process illustrated in FIG. 6, a carbon oxide containing natural gas (610) is passed over a hydrocarbon synthesis catalyst in a hydrocarbon synthesis step (240), for converting at least a portion of the carbon oxides in the natural gas to hydrocarbons. An exemplary hydrocarbon product in this reaction is methane. Thermal energy (270) produced during hydrocarbon synthesis is passed to an electrolysis step (180). Natural gas (620) depleted in carbon oxides is produced from the hydrocarbon synthesis. In one embodiment, the carbon oxide depleted natural gas (620) is passed to a liquefaction process for converting the natural gas to liquefied natural gas. At least a portion of the hydrogen (190) which is provided to the hydrocarbon synthesis step is generated from electrolysis (180) of water or a brine solution (185). At least a portion of the thermal energy (150) for operating the electrolysis process (180) at elevated temperature is provided from a reaction of flue gas (630) over an active metal (130) in a metal oxidation process (120). The carbon oxides in the flue gas react with the active metal, forming a metal oxide and capturing the carbon in the carbon oxides as molecular carbon and/or CO (170). In one embodiment, a portion of the thermal energy (270) generated from the hydrocarbon synthesis reaction (240) is provided to the electrolysis process (180).

Example 7

In the exemplary process illustrated in FIG. 7, a carbon oxide containing fluid (110) is passed over an active metal (130) in a metal oxidation step (120), for converting the metal to a metal oxide (160), and for capturing the carbon in the carbon oxides as molecular carbon, and/or $CO_2$ to CO (170). Integral in the metal oxidation process is an electrolysis process (180) for the high temperature electrolysis of water or brine. Heat generated in the metal oxidation step is directly available to the electrolysis step. In one embodiment, the oxidation and electrolysis are conducted in a shell and tube system, with one of the oxidation or electrolysis being conducted on the shell side of the system, and the other process, oxidation or electrolysis, being conducted within the tubes of the system. Hydrogen (190) generated in the electrolysis portion of the integral process is available for reacting with other portions of carbon oxides in a hydrocarbon synthesis process to generate additional amounts of methane in the process.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as that term is interpreted as a transitional word in a claim.

What is claimed is:

1. A process for reducing the carbon oxides content in natural gas, comprising:
   a. producing a carbon oxides containing natural gas from a geological formation through a natural gas delivery system;
   b. providing a reaction zone containing at least one catalyst suitable for hydrocarbon conversion in the natural gas delivery system;
   c. introducing hydrogen into the carbon oxides containing natural gas to form a reaction mixture; and
   d. passing the reaction mixture to the catalyst in the reaction zone to convert at least a portion of the carbon oxides in the natural gas to hydrocarbons.

2. The process of claim 1, further comprising passing the reaction mixture to the catalyst in the reaction zone to convert at least a portion of the carbon oxides in the natural gas to methane.

3. The process of claim 1, further comprising passing the reaction mixture to the catalyst in the reaction zone to convert at least a portion of the carbon oxides in the natural gas to a mixture of paraffins and alcohols.

4. The process of claim 1, further comprising passing the reaction mixture to the catalyst in the reaction zone to perform a water gas shift reaction over a water gas shift catalyst.

5. The process of claim 1, further comprising passing the reaction mixture to the catalyst in the reaction zone to convert at least a portion of the carbon oxides in the natural gas to methane and passing the natural gas in combination with the methane to a liquefaction process.

6. The process of claim 1, wherein the carbon oxides comprises $CO_2$ and further comprising passing the reaction mixture to the catalyst in the reaction zone to convert at least a portion of the $CO_2$ in the natural gas to CO.

7. An integrated process for reducing the carbon oxides content in natural gas, comprising:
   a. producing a carbon oxides containing natural gas from a geological formation through a natural gas delivery system;
   b. providing a reaction zone comprising at least one catalyst suitable for hydrocarbon conversion in the natural gas delivery system;
   c. introducing hydrogen into the carbon oxides containing natural gas to form a reaction mixture; and
   d. passing the reaction mixture to the catalyst in the reaction zone to convert at least a portion of the carbon oxides in the natural gas to methane in a hydrocarbon synthesis step.

8. The process of claim 7 wherein at least a portion of the carbon oxides in the natural gas are converted to a mixture of paraffins and alcohols.

9. The process of claim 7, further comprising performing a water gas shift reaction over a water gas shift catalyst.

10. The process of claim 7, further comprising passing the natural gas in combination with the methane to a liquefaction process.

11. The process of claim 7, wherein the carbon oxides comprise $CO_2$ and wherein at least a portion of the $CO_2$ in the natural gas is converted to CO.

12. The process of claim 7, further comprising
   e. separating at least a portion of carbon oxides remaining in the natural gas following the hydrocarbon synthesis step into a carbon oxide rich fluid;
   f. supplying the carbon oxide rich fluid to a metal oxidation step, and reacting at least a portion of the carbon oxides with an active metal at an elevated temperature; and
   g. supplying at least a portion of the thermal energy produced during the metal oxidation step to a hydrogen recovery process.

13. The process of claim 12 wherein the hydrogen recovery process comprises an electrolysis.

14. An integrated process for reducing the carbon oxides content in natural gas, comprising:
   a. producing a carbon oxides containing natural gas from a geological formation through a natural gas delivery system;
   b. providing a reaction zone comprising at least one catalyst suitable for hydrocarbon conversion in the natural gas delivery system;
   c. introducing hydrogen into the carbon oxides containing natural gas to form a reaction mixture; and
   d. passing the reaction mixture to the catalyst in the reaction zone to convert at least a portion of the carbon oxides in the natural gas to one or more hydrocarbons in a hydrocarbon synthesis step;
   e. separating at least a portion of carbon oxides remaining in the natural gas following the hydrocarbon synthesis step into a carbon oxides rich fluid;
   f. supplying the carbon oxides rich fluid to a metal oxidation step, and reacting at least a portion of the carbon oxides with an active metal at an elevated temperature; and
   g. supplying at least a portion of the thermal energy produced during the metal oxidation step to an electrolysis process for recovering hydrogen used to form the reaction mixture.

15. The process of claim 14 wherein at least a portion of the carbon oxides in the natural gas are converted to methane.

16. The process of claim 14 wherein at least a portion of the carbon oxides in the natural gas are converted to a mixture of paraffins and alcohols.

17. The process of claim 14, further comprising passing the reaction mixture to the catalyst in the reaction zone to perform a water gas shift reaction over a water gas shift catalyst.

18. The process of claim 14, further comprising passing the reaction mixture to the catalyst in the reaction zone to convert at least a portion of the carbon oxides in the natural gas to methane and passing the natural gas in combination with the methane to a liquefaction process.

19. The process of claim 14, wherein the carbon oxides comprise $CO_2$ and wherein at least a portion of the $CO_2$ in the natural gas is converted to CO.

* * * * *